United States Patent [19]
Richardson et al.

[11] Patent Number: 5,377,237
[45] Date of Patent: Dec. 27, 1994

[54] METHOD OF INSPECTING REPAIRED STUB TUBES IN BOILING WATER NUCLEAR REACTORS

[75] Inventors: David L. Richardson, Los Gatos; James C. S. Tung, San Jose; James H. Terhune, San Jose; Gerald A. Deaver, San Jose, all of Calif.

[73] Assignee: General Electric Company, San Jose, Calif.

[21] Appl. No.: 43,053

[22] Filed: Apr. 5, 1993

[51] Int. Cl.$^5$ .............................................. G21C 17/00
[52] U.S. Cl. ................................... 376/252; 376/249; 376/245
[58] Field of Search ............... 376/252, 249, 245, 291, 376/292, 263, 203; 73/598, 588, 600; 976/DIG. 214

[56] References Cited

U.S. PATENT DOCUMENTS

| | | | |
|---|---|---|---|
| 4,252,022 | 2/1981 | Hurwitz | 73/582 |
| 4,548,785 | 10/1985 | Richardson et al. | 376/249 |
| 4,593,568 | 6/1986 | Telford et al. | 73/623 |
| 4,770,105 | 9/1988 | Takagi et al. | 104/138.2 |
| 4,856,337 | 8/1989 | Metala et al. | 73/601 |
| 4,955,235 | 9/1990 | Metala et al. | 73/601 |
| 5,118,464 | 6/1992 | Richardson et al. | 376/252 |
| 5,145,637 | 9/1992 | Richardson et al. | 376/249 |
| 5,267,481 | 12/1993 | Smith | 73/623 |
| 5,272,734 | 12/1993 | Clark et al. | 376/260 |

Primary Examiner—Donald P. Walsh
Assistant Examiner—Meena Chelliah
Attorney, Agent, or Firm—J. E. McGinness

[57] ABSTRACT

An ultrasonic method of inspecting repaired stub tubes in a boiling water reactor. The top and bottom ends of each stub tube are respectively welded to the corresponding control rod drive housing and to the bottom head of the reactor pressure vessel. Under certain conditions, a crack can form in the heat-affected zone of the stub tube adjacent to the upper weld, necessitating repair by installing a mechanical seal. A probe inserted in the control rod drive housing has transducers which transmit pulsed ultrasonic energy toward a machined surface-air gap interface disposed to reflect the pulse trains generally axially through the stub tube. The radial and azimuthal dimensions of a radial crack in the stub tube are determined in dependence on which pulsed trains are reflected back to the probe by the crack via the interface.

10 Claims, 3 Drawing Sheets

METHOD OF INSPECTING REPAIRED STUB TUBES IN BOILING WATER NUCLEAR REACTORS

FIELD OF THE INVENTION

This invention relates generally to nondestructive examination of material, such as metal, for voids, flaws, cracks and other defects that can be detrimental to the integrity of the material. Specifically, the invention relates to the ultrasonic inspection of stub tube components following their repair in nuclear power reactors of the boiling water type.

BACKGROUND OF THE INVENTION

The structure of a water-cooled and water-moderated nuclear reactor of the boiling water type is well known. (See, for example, U.S. Pat. Nos. 4,548,785 and 5,118,464 to Richardson et al.) A boiling water reactor includes a pressure vessel containing a nuclear reactor core submerged in a coolant-moderator such as light water. The core, which is surrounded by an annular shroud, includes a plurality of replaceable fuel assemblies arranged in spaced relation between an upper core grid and a lower core plate.

A plurality of control rod drive housings penetrate the pressure vessel and house control rod drives by which a plurality of control rods are selectively insertable among the fuel assemblies for controlling the core reactivity. The control rod drive housings support control rod guide tubes which receive and house the control rods when they are withdrawn from the core. The guide tubes, in turn, support fuel assembly support members, each of which is formed with sockets for receiving the nose pieces of four adjacent fuel assemblies.

Each control rod and the four fuel assemblies comprise a fuel cell of the core. The four fuel assemblies are laterally supported at their upper ends in an opening in the upper core grid formed by intersecting and interlocking beams. At their lower ends the four fuel assemblies are vertically supported on the fuel assembly support member fitted to the top end of the control rod guide tube, lateral support being provided by passage of the guide tube through an aperture or hole in the lower core plate.

Penetration of the control rod drive housings through the bottom head of the reactor pressure vessel is accomplished using stub tubes. Each stub tube, suitably shaped at its bottom end to fit the curvature of the bottom head at its particular location, is secured in a corresponding aperture or hole in the bottom head by a circumferential weld. The need for precise positioning of the stub tube is avoided by finish boring of its inside diameter, after it is welded in place, to receive the control rod drive housing. The control rod drive housing is welded to the top end of the stub tube after the control rod drive housing is properly positioned vertically with all of the top ends of the control rod drive housings in the same horizontal plane. This means that the control rod drive housings extend into the reactor pressure vessel by varying amounts because of the curvature of the bottom head thereof.

As is evident from the foregoing, the stub tubes become a part of the pressure vessel boundary and any defect (e.g., cracks) therein can jeopardize the integrity of the pressure system. Under certain conditions, the stub tubes are found to undergo stress corrosion cracking in the heat-affected zone adjacent to the upper weld joining the control drive rod housing and the stub tube. This stress corrosion cracking may result in water leakage from the vessel through the narrow gap between the control drive rod housing and the stub tube, an undesirable event necessitating repair.

The conventional means of repairing faulted stub tubes is to "cap" them in such a way as to prevent leakage. After repair, it is necessary to monitor known cracks for growth following subsequent reactor operation. In general, inspection of repaired tubes from the outside surface, i.e., from the surface facing inside the vessel, is not practical because of limited access. U.S. Pat. No. 5,118,464 discloses a method for inspecting stub tubes from the inside surface of the control rod drive housing utilizing ultrasound transmitted through and bridging a narrow circumferential gap between the control drive rod housing and the stub tube. This method requires under-vessel fixtures to control the ultrasonic medium in the gap. For practical reasons, this is not always possible.

SUMMARY OF THE INVENTION

Ultrasound is a common means of nondestructively inspecting materials for flaws and structural integrity. For steels, the preferred frequency used for inspection and sizing of flaws is in the range of 1 to 10 MHz with 2.25 to 5 MHz preferred. Ultrasonic transducers and associated electronics are conventional in the art of nondestructive examination.

In accordance with conventional practice, pulsed ultrasound generated by a transducer propagates into the metal to be inspected via a coupling fluid, such as water, in contact with the surface of the metal. Discontinuities in the metal (e.g., cracks) produce ultrasonic pulse reflections, due to sudden changes in acoustic impedance, that are dependent on factors such as flaw size and shape, angle of incidence, and metal path length. These reflections are detected by ultrasonic transducers operating in a reception mode.

An important property of the interaction of ultrasonic energy with regular, smooth surfaces bounded by an abrupt change in acoustic impedance is adherence to the law of specular reflection, known in optics as Snell's Law. The present invention utilizes the properties of ultrasonic pulse propagation and reflection to effectively and remotely detect and measure crack properties in otherwise inaccessible areas of repaired stub tubes. In particular, specular reflection is used in the present invention to direct pulsed ultrasound to crack zones located under the "cap" of repaired stub tubes. This technique allows for inspection and monitoring, from inside the control rod drive housing, of the status of crack propagation (i.e., crack growth) and prediction of the structural integrity of the repaired member.

In accordance with the method of the invention, certain surface areas are prepared to a 45° "mirror finish" by electrodischarge machining prior to application of the seal. A mechanical seal used to cap the stub tube is installed so that an air gap is formed between the "mirror finish" machined surface and an opposing surface of the mechanical seal. This air gap can be designed to act as an efficient reflector of ultrasound, e.g., by ensuring that the conditions for forming a standing ultrasonic wave in the gap are not satisfied. The conditions for forming a standing wave in a gas gap are described in U.S. Pat. No. 5,118,464 to Richardson et al.

An ultrasonic probe having an array of transducers is positioned inside the control rod drive housing. The transducers are arranged to transmit pulsed ultrasound through the control rod drive housing and along a path such that the ultrasound impinges on the machined surface. The ultrasound is reflected at the interface between the machined surface and the air gap. These reflected pulses propagate axially through the stub tube. Any radial crack in the path of propagation of the ultrasound will reflect the ultrasonic pulses back to the machined surface-air gap interface. The interface then reflects the impinging ultrasonic pulses back to the probe. The ultrasonic transducers operate in a reception mode during the expected time of arrival of the echo, outputting suitable electrical signals for subsequent processing in response to detection of the echoes.

In accordance with the method of the invention, the probe is located inside the control rod drive housing to access the stub tube without the necessity of traversing the gap between the control rod drive housing and stub tube. Preferably, the probe employs a linear array of transducers which scan the stub tube cross section. In the preferred embodiment, the transducers are distributed at equal intervals along a vertical line and are activated in sequence to provide a means for measuring the radial dimensions of cracks of arbitrary shape and orientation. To enable scanning of the stub tube in the azimuthal direction, the probe is driven to rotate in stepwise fashion by a conventional tool rotary drive mechanism.

In addition, the invention utilizes multi-path and multi-reflection principles to monitor nonplanar or branched cracks, or cracks whose faces are not perpendicular to the stub tube surfaces. The invention further utilizes multi-mode and mode-conversion means to detect and measure nonuniform or steeply oriented cracks.

The method of the invention is especially useful in detecting and measuring cracks in cap-sealed stub tubes, where accessibility from inside the reactor pressure vessel is limited or poor. Thus, the method of the invention enables inspection of zones of the stub tube which may be susceptible to stress corrosion cracking during reactor operation.

DETAILED DESCRIPTION OF THE PREFERRED EMBODIMENTS

The invention is described herein as applied to the examination of repaired stub tubes in a nuclear reactor. However, an artisan of ordinary skill in the art of nondestructive examination will readily appreciate that the method of the invention is applicable to the detection of cracks in any cylindrical component the inside of which can be readily accessed.

Figure 1:
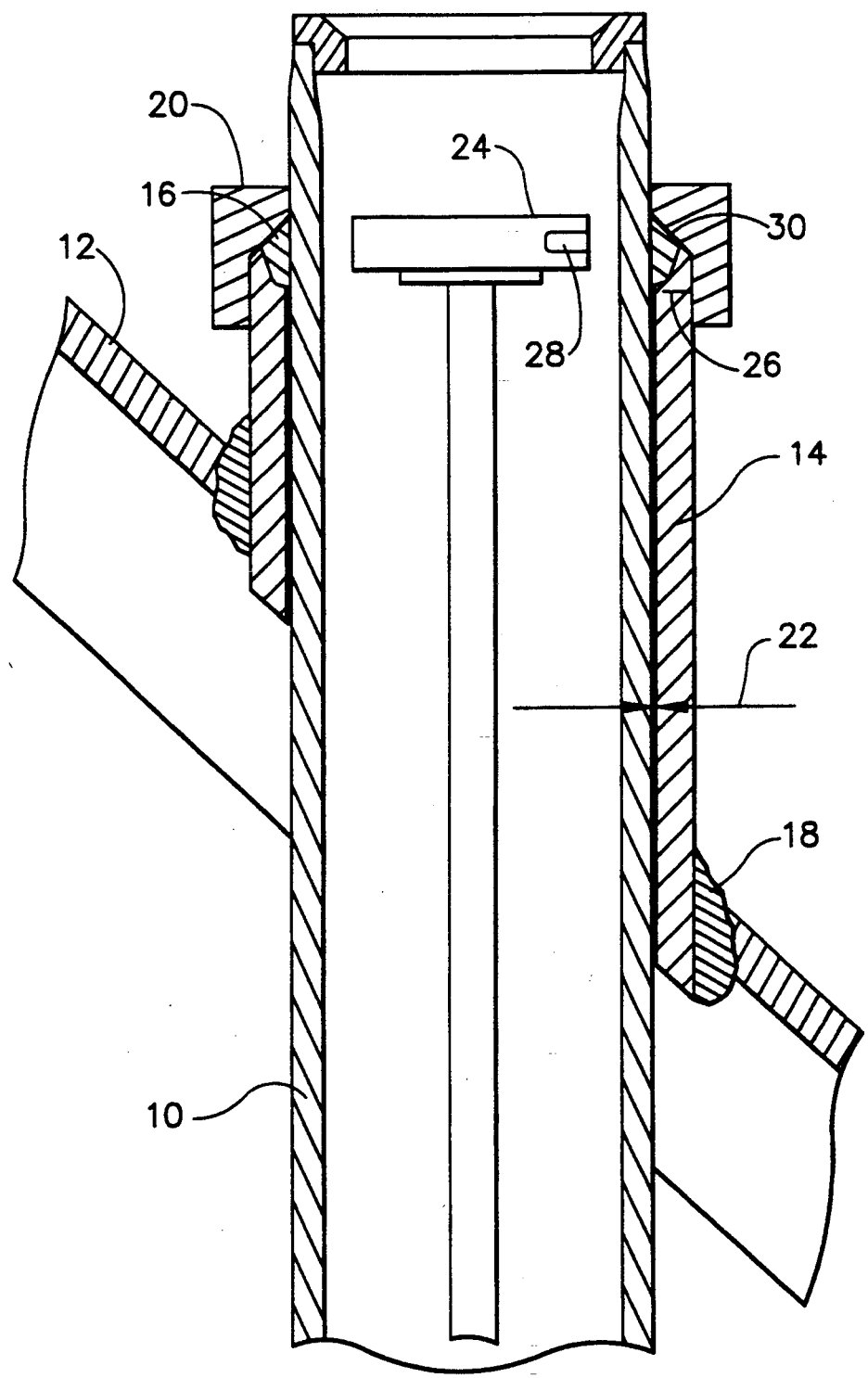
FIG. 1 is a schematic representation of an inspection tool containing an ultrasonic probe head assembly for directing pulsed ultrasonic energy into the cap-sealed region of a cracked stub tube and detecting energy reflected by the crack in accordance with the method of the invention.

As shown in FIG. 1, each control rod drive housing 10 is a tube which passes through the bottom head 12 of the reactor pressure vessel. The control rod drive housing 10 is supported by a stub tube 14. At its top end, stub tube 14 is joined to control rod drive housing 10 by an upper attachment weld 16. At its bottom end, stub tube 14 is joined to bottom head 12 by a lower attachment weld 18. The stub tube 14 and control rod drive housing 10 are separated by a circumferential gap 22. The exact dimension of gap 22 at any given location cannot be precisely known, but generally will vary from metal-to-metal contact (i.e., zero gap) to about 15 mils.

Figure 3:
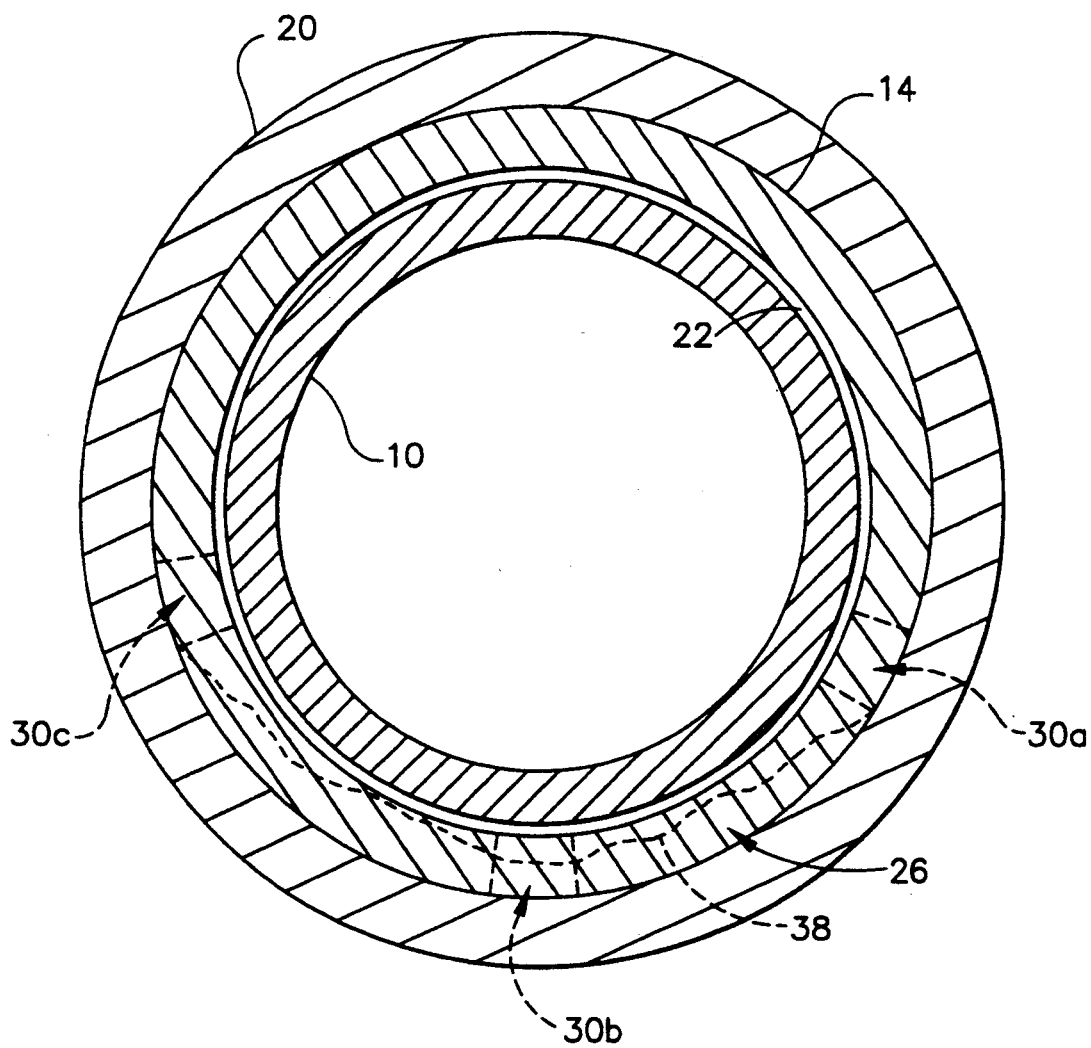
FIG. 3 is a sectional view taken along line 3—3 shown in FIG. 2.

Experience has shown that the heat-affected zone of the stub tube adjacent to upper weld 16 is susceptible to stress corrosion cracking. A radially inwardly propagating crack 26 of this type, having a propagating front represented by dashed line 38, is best seen in FIG. 3. The conditions of metallic tension, stagnation of water flow and oxygen concentration cause the crack front 38 to propagate along the granular boundaries of the metal. Ultimately, the crack 26 could propagate to the inner surface of the stub tube, whereat the crack is in fluid communication with gap 22, thereby creating a flow path for water to escape from the reactor pressure vessel.

Figure 2:
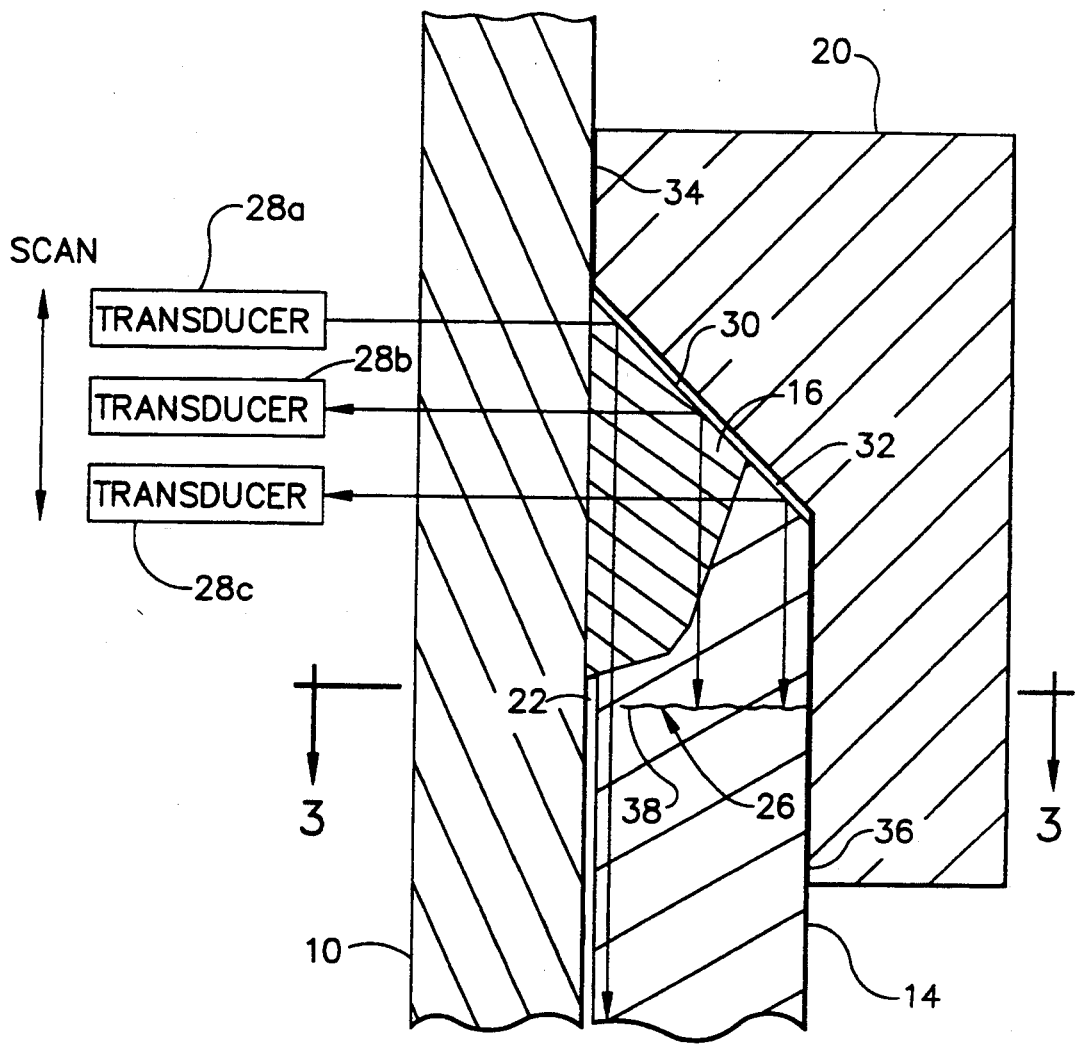
FIG. 2 is a schematic representation of a repaired stub tube with a mechanical seal in place, the arrows showing the principle of operation by which cracks are detected and monitored in accordance with the method of the invention.

Stub tubes having cracks in the heat-affected zone adjacent to the upper weld are conventionally repaired by installing a mechanical seal 20. As best seen in FIG. 2, mechanical seal 20 has a first inner circumferential surface, of diameter slightly greater than the diameter of control rod drive housing 10, which is sealed to the latter via a carbon seal 34, and a second inner circumferential surface, of diameter slightly greater than the diameter of stub tube 14, which is sealed to the latter via a carbon seal 36.

Before the mechanical seal is installed, a plurality of monitor areas 30 are formed on the stub tube and upper weld (see FIG. 2). Each monitor area 30 is a planar surface prepared to a 45° "mirror finish" by electrodischarge machining. Mechanical seal 20 is installed so that a small air gap 32 is formed between the "mirror finish" machined surface and an opposing surface of the mechanical seal. This air gap can be designed to act as an efficient reflector of ultrasound.

The method of the invention is carried out using a probe head 24 (see FIG. 1) having a multiplicity of transducers 28 specifically arranged for the purpose of monitoring the radial extent of cracks in the stub tube. In accordance with one preferred embodiment, the probe employs a vertical linear array of transducers 28$a$, 28$b$, 28$c$ (see FIG. 2) which are activated in sequence to scan the stub tube cross section in a radial plane. The transducers are aligned to transmit pulsed ultrasound along parallel paths of propagation.

Each machined surface-air gap interface 30 is preferably a conical surface having a common axis with stub tube 14. In accordance with the law of reflection, the respective pulsed trains of ultrasound transmitted by the transducers and reflected by interface 30 propagate axially through the stub tube at increasing radii as the transducers in the vertical linear array are activated in succession from top to bottom.

FIG. 2 depicts a radial crack 26 which reflects the pulsed trains of ultrasonic radiation transmitted by transducers 28$b$ and 28$c$ and reflected by the machined surface-air gap interface 30 and which does not reflect the pulsed train of ultrasonic radiation transmitted by transducer 28$a$ and reflected by interface 30. By detecting which pulsed trains are reflected, the radial extent or depth of crack 26 at a first azimuth angle can be determined.

Thereafter, the probe head can be rotated to a second azimuth angle corresponding to the angular position of the next monitor area. The linear array of transducers are activated in sequence anew, the echoes enabling the radial extent or depth of crack 26 at the second azimuth angle to be determined. The probe is driven to rotate by a conventional tool rotary drive mechanism (not shown).

Thus, as the transducers scan the cross section of the stub tube in a radial plane, the planar, flat crack 26 (best seen in FIG. 3) reflects ultrasonic energy back to the probe, thereby indicating the extent of the flaw in that radial plane. In the case where the crack front 38 has not reached the inner wall of the stub tube 14 (as depicted in FIG. 3), there is a zone of nonreflectance indicative of the crack depth, or extent, into the metal.

In practice, it is not necessary to monitor all of the crack, but only certain zones of it. The azimuthal positions of exemplary monitor zones are indicated by dashed lines in FIG. 3. The monitoring areas 30a, 30b, 30c are machined into the upper weld-stub tube top surface by electrodischarge machining. Preferably the machined surfaces are formed as generated conical surfaces disposed at an angle of 45° relative to the stub tube axis. However, angles other than 45° can be used provided that the direction of transmission of the transducers is suitably adjusted to ensure that pulsed trains of ultrasound reflected by the machined surface-air gap interface will propagate axially through the stub tube, thereby allowing the ultrasound to access the crack ends, or tips. This in turn enables monitoring of azimuthal crack growth, which is the major concern in operating with repaired stub tubes. The number of monitor areas, or zones, is arbitrary, although a minimum of three is preferred. In fact, the entire upper weld could be machined, but this is expensive and time-consuming.

In practice, cracks may not be regular, or planar. In such case, only a fraction of the incident energy will be reflected back to the transducers. However, the gap 22 between control rod drive housing 10 and stub tube 14 also serves as a reflector. Therefore, gap 22 can redirect ultrasonic energy from a crack surface cocked downward relative to the crack shown in FIG. 2. Likewise, that portion of the interface between stub tube 14 and mechanical seal 20 which lies above the crack 26 can be machined to serve as a good reflector for ultrasonic energy reflected from a crack surface cocked upward. Therefore, by proper design, the method of the invention can be effective without special considerations of the crack size, shape or orientation.

A preferred mode of pulse propagation is the longitudinal mode. This allows for discrimination against unwanted mode conversion to shear waves at the reflecting surfaces, since the latter travel at lower velocity and can be time-gated out of the data. However, certain crack orientations may be more accessible using mode-converted shear waves that are also reflected by mirror surfaces. Therefore, in accordance with the method of the invention, either longitudinal or shear waves can be utilized.

Although the method of the invention has been disclosed in the context of a vertical linear array of transducers which are rotated in stepwise fashion, other arrangements can be readily used. For example, the method of the invention can be carried out using a probe having a single transducer which is vertically displaced in a stepwise manner to scan a radial plane through the stub tube. All such variations and modifications are intended to be encompassed by the claims set forth hereinafter.

We claim:

1. A method for detecting a generally radially disposed crack in a stub tube joined to a control rod drive housing by a weld, said stub tube and said control rod drive housing having an air gap therebetween located below said weld, comprising the steps of:

machining contiguous surface areas on said stub tube and said weld to form a first smooth surface which is a portion of a conical surface generally coaxial with the axis of said stub tube;

installing a mechanical seal having a first inner circumferential surface sealed to an outer circumferential surface of said control rod drive housing and a second inner circumferential surface sealed to an outer circumferential surface of said stub tube, said mechanical seal being positioned so that an air gap is formed between said mechanical seal and said first smooth surface, the boundary between said first smooth surface and said air gap forming a first interface which reflects ultrasonic energy impinging thereon;

placing ultrasonic transducer means inside said control rod drive housing;

transmitting pulsed ultrasonic energy from said ultrasonic transducer means toward said first interface at a predetermined angle relative thereto such that said first interface reflects said pulsed ultrasonic energy in a generally axial direction through a first generally radial plane of said stub tube; and detecting pulsed ultrasonic energy reflected by said crack and impinging on said ultrasonic transducer means.

2. The method as defined in claim 1, wherein said ultrasonic transducer means comprises a plurality of transducers arranged in a linear array and directed to transmit pulsed ultrasonic energy along parallel paths, each transducer being positioned at a different elevation, said transducers being activated in a predetermined sequence, whereby the cross section of said stub tube is scanned in said first generally radial plane.

3. The method as defined in claim 1, wherein the boundary between said control rod drive housing and said weld forms an interface which does not reflect ultrasonic energy, said pulsed ultrasonic energy propagating through said nonreflective interface before impinging on said first interface.

4. The method as defined in claim 1, wherein said ultrasonic transducer means transmits first and second trains of pulsed ultrasonic energy in sequence along mutually parallel first and second paths of propagation intersecting said first interface, said first interface being disposed to reflect said first and second trains of pulsed ultrasonic energy along mutually parallel third and fourth paths of propagation in a generally axial direction through said stub tube, said third and fourth propagation paths lying in said first generally radial plane.

5. The method as defined in claim 1, further comprising the steps of:

before said step of installing said mechanical seal, machining contiguous surface areas on said stub tube and said weld to form a second smooth surface which is a portion of a conical surface generally coaxial with the axis of said stub tube, said mechanical seal being positioned so that an air gap is formed between said mechanical seal and said second smooth surface, the boundary between said second smooth surface and said air gap forming a second interface which reflects ultrasonic energy impinging thereon, said first and second interfaces being separated by a predetermined azimuth angle;

rotating said ultrasonic transducer means by said predetermined azimuth angle;

transmitting pulsed ultrasonic energy from said ultrasonic transducer means toward said second interface at a predetermined angle relative thereto such that said second interface reflects said pulsed ultrasonic energy in a generally axial direction through a second generally radial plane of said stub tube; and detecting pulsed ultrasonic energy reflected by said crack which impinges on said ultrasonic transducer means.

6. The method as defined in claim 5, wherein said ultrasonic transducer means transmits third and fourth trains of pulsed ultrasonic energy in sequence along mutually parallel fifth and sixth paths of propagation intersecting said second interface, said second interface being disposed to reflect said third and fourth trains of pulsed ultrasonic energy along mutually parallel seventh and eighth paths of propagation in a generally axial direction through said stub tube, said seventh and eighth propagation paths lying in said second generally radial plane.

7. In an arrangement for monitoring a crack in a repaired stub tube, comprising a control rod drive housing, a stub tube surrounding a portion of said control rod drive housing, a circumferential weld joining said stub tube to said control rod drive housing, said stub tube and said control rod drive housing having an air gap therebetween located below said circumferential weld, and a mechanical seal capping said circumferential weld, said mechanical seal having a first inner circumferential surface sealed to an outer circumferential surface of said control rod drive housing and a second inner circumferential surface sealed to an outer circumferential surface of said stub tube, the improvement wherein contiguous surface areas on said stub tube and said circumferential weld are machined to form a first smooth surface which is a portion of a conical surface generally coaxial with the axis of said stub tube, said mechanical seal having a surface opposing said first smooth surface with an air gap therebetween, the boundary between said first smooth surface and said air gap forming a first interface for reflecting ultrasonic energy impinging thereon.

8. The crack monitoring arrangement as defined in claim 7, further comprising a plurality of transducers arranged in a linear array and directed to transmit pulsed ultrasonic energy along parallel paths, each transducer being positioned at a different elevation, said transducers being activated in a predetermined sequence, whereby the cross section of said stub tube is scanned in a generally radial plane by ultrasonic energy reflected by said first interface.

9. The crack monitoring arrangement as defined in claim 7, wherein contiguous surface areas on said stub tube and said circumferential weld are machined to form a second smooth surface which is a portion of a conical surface generally coaxial with the axis of said stub tube, said mechanical seal having a surface opposing said second smooth surface with an air gap therebetween, said first and second smooth surfaces being separated by a predetermined azimuth angle, the boundary between said second smooth surface and said air gap forming a second interface for reflecting ultrasonic energy impinging thereon.

10. The crack monitoring arrangement as defined in claim 9, further comprising ultrasonic transducer means positioned inside said control rod drive housing, said ultrasonic transducer means having a first angular position at which pulsed ultrasonic energy is transmitted toward said first interface, said first interface reflecting said pulsed ultrasonic energy in a generally axial direction and in a first generally radial plane of said stub tube, and a second angular position at which pulsed ultrasonic energy is transmitted toward said second interface, said second interface reflecting said pulsed ultrasonic energy in a generally axial direction and in a second generally radial plane of said stub tube, said first and second generally radial planes being separated by said predetermined azimuth angle.

* * * * *